United States Patent [19]

Jadow

[11] 4,407,310

[45] Oct. 4, 1983

[54] SCULPTURED ARTIFICIAL NAIL

[75] Inventor: Henry C. Jadow, New York, N.Y.

[73] Assignee: Kristy Wells, Inc., New York, N.Y.

[21] Appl. No.: 157,039

[22] Filed: Jun. 6, 1980

Related U.S. Application Data

[63] Continuation-in-part of Ser. No. 913,566, Jun. 8, 1978, abandoned, which is a continuation-in-part of Ser. No. 872,502, Jan. 26, 1978, abandoned.

[51] Int. Cl.³ ............................................. A45D 29/00
[52] U.S. Cl. ........................................ 132/73; 424/61
[58] Field of Search ...................... 132/73, 89; 424/61

[56] References Cited

U.S. PATENT DOCUMENTS

| | | | |
|---|---|---|---|
| 2,073,867 | 3/1937 | Feigenbaum | 132/73 |
| 2,746,460 | 5/1957 | Jellinek | 132/73 |
| 3,856,026 | 12/1974 | Gaydos | 132/73 |
| 4,007,748 | 2/1977 | Matranga | 132/73 |
| 4,135,526 | 1/1979 | Matranga | 132/73 |
| 4,157,095 | 6/1979 | Sweet | 132/73 |

Primary Examiner—Gregory E. McNeill
Attorney, Agent, or Firm—Cooper, Dunham, Clark, Griffin & Moran

[57] ABSTRACT

An artificial nail for repairing, strengthening or sculpturing of a natural nail. The artificial nail includes a granular material such as glass beads which is adhesively bonded with a bonding composition such as cyanoacrylate glue to the natural nail to form a textured surface. If desired, textured layers, also composed of the granular material and bonding composition, may be adhesively bonded to the textured surface of the natural nail to provide for an artificial nail of the desired thickness. The artificial nail is shaped with a nail file and buffed to its final form.

7 Claims, 12 Drawing Figures

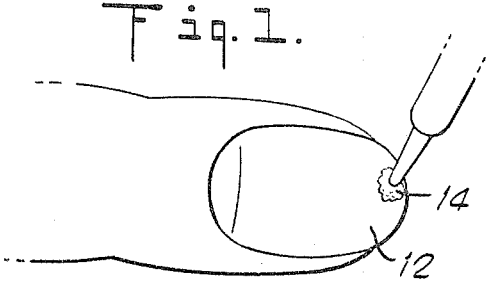
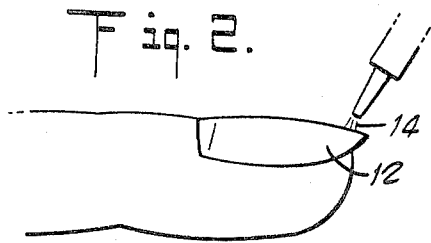
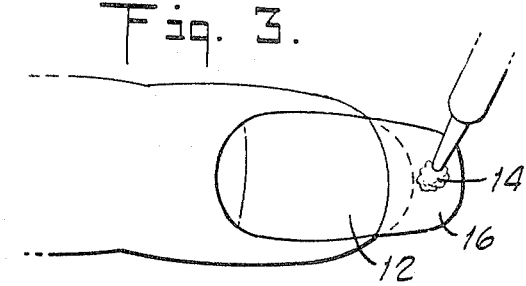
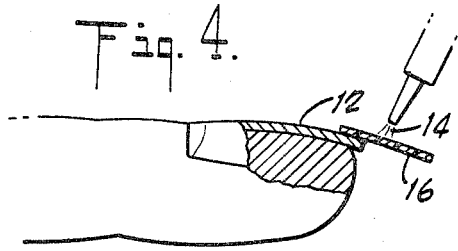
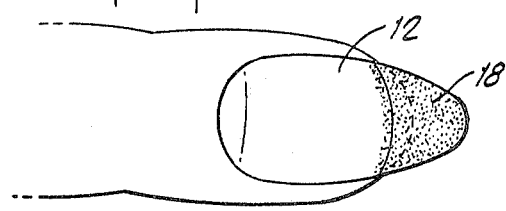
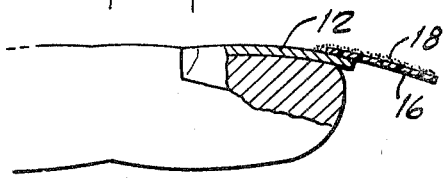
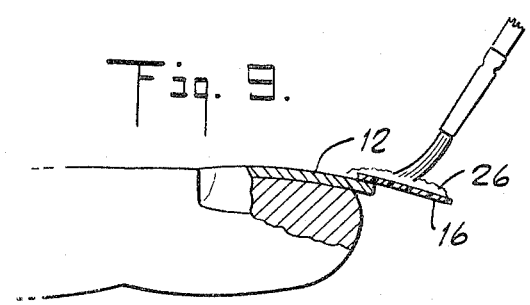
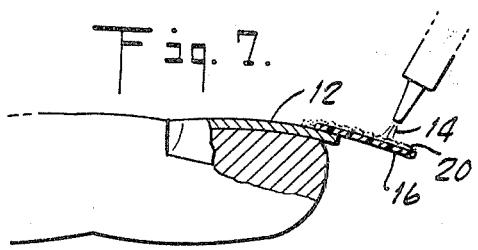
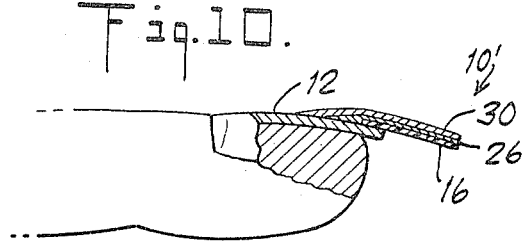
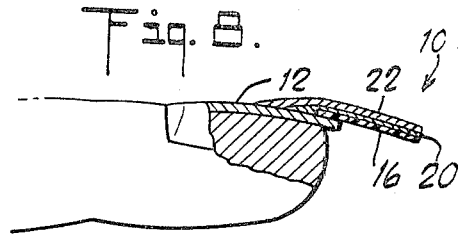

SCULPTURED ARTIFICIAL NAIL

REFERENCE RELATED APPLICATIONS

This application is a continuation-in-part of Patent Application Ser. No. 913,566, filed June 8, 1978 now abandoned, which is a continuation-in-part of Patent Application Ser. No. 872,502, filed Jan. 26, 1978 now abandoned, which are both hereby incorporated by reference.

BACKGROUND AND SUMMARY OF THE INVENTION

The invention is related to artificial nail structures for attachment to and lengthening of and for repairing, strengthening or sculpturing of natural nails. It is particularly concerned with a sculptured artificial nail that is inexpensive and that may be easily applied to the natural nail of a user.

There are various prior art artificial nail structures for attachment to and lengthening of natural nails. Examples are described in Matranga et al., U.S. Pat. No. 4,007,748; Michaelson et al., U.S. Pat. No. 3,552,401; Jarby, U.S. Pat. No. 3,502,088; Sautter et al., U.S. Pat. No. 3,478,756; Feigenbaum, U.S. Pat. No. 2,073,867 and an article, "Service Equals Profits With New Nail Care Techniques", *Modern Beauty Shop*, dated April 1976, pp. 75–78. While often useful, such prior art structures may have several disadvantages. For example, the prior art structures known to applicant which have been used commercially may, for the purpose of illustration, be classified into several different types. A first type, a solid artificial nail, commonly known as "nail shells", comprises a preformed, i.e., conforming as nearly as possible to the shape of the natural nail to which it will be attached, solid plastic material adhesively bonded with glue to the natural nail. Nail shells are disposed over substantially the entire natural nail. The disadvantages of using nail shells are that: they must be removed periodically, usually within 24 to 48 hours, since they tend to damage the natural nail in that they do not allow the natural nail to "breathe", i.e., they cause fungus infections; the natural nail grows underneath the artificial nail and thus may cause the artificial nail to pop off and/or to damage the natural nail; the nail shells are normally manufactured from plastics that are flammable; the user tends to lose normal touch sensation of the natural nail so that the nails feel dead at their outwardly extending ends; and the nail shells may be dislodged easily from the natural nail when the user does normal household chores.

Another type of artificial nail, normally sold in a kit, comprises a powdered acrylic polymer, a liquid acrylic monomer and a set of adhesive backed forms. The form serves as a base and is disposed under the natural nail so as to cover the sides and project beyond the naturally extending end thereof. The polymer and monomer are mixed and applied to the natural nail and the projecting portion of the form serving as the base. The form is removed after the polymer/monomer mixture dries and is of the desired thickness. This type of artificial nail is referred to as a "porcelain nail". The disadvantages of the porcelain nail are that: the porcelain nail covers substantially the entire natural nail since in practice the polymer/monomer mixture is difficult to apply in a precise manner and consequently must be tapered over the length of the natural nail so as to smooth out the formation of a ridge where the natural nail ends and the artificial nail begins; the natural nail grows underneath the artificial nail and may cause the artificial nail to pop off and/or to damage the natural nail; the artificial nail may pop off in cold water and in normal household and work usage; the artificial nail is flammable; the user may experience a loss of touch sensation or may have an allergic reaction due to the porcelain nail.

A variation on the porcelain nail technique provides for initially placing a piece of wax paper over substantially the entire natural nail. A monomer/polymer mixture is applied over the wax paper and after the mixture dries, the artificial nail formed is removed and adhesively bonded to the natural nail, in an overlapping manner, by means of cyanoacrylate glue. The disadvantages of this modified porcelain nail are that: the artificial nail is difficult to form; it is flammable; and a two-step process is required.

A further type of artificial nail, as disclosed in the Matranga et al. patent, consists of a preformed plastic form which is applied to the outwardly extending end of the natural nail, edge to edge or with a slight overlap, by means of cyanoacrylate glue. The disadvantages of this artificial nail are that: the application of the artificial nail requires a considerable amount of manual dexterity; the artificial nail is soluble in acetone, i.e., nail polish remover, and if a slight excess is applied to remove old nail polish, the artificial nail weakens and becomes soft or falls off; it is difficult to smooth out the joint formed between the natural nail and the artificial nail; and the artificial nail does not extend the natural curvature of the natural nail.

In view of this prior art, there is a need for an artificial nail structure which may be quickly applied by a user requiring little manual dexterity, which can be made extremely strong and will not be damaged by household or office work, which is inflammable, which does not require preformed shapes, which is permanent and need not even be removed periodically, since the entire natural nail or even a substantial portion thereof need not be covered so that it may be allowed to "breathe", which requires no mixing of chemicals and minimizes any allergic reaction by the user, which preserves touch sensation, and extends the natural curvature of the nail. Such structure should also be inexpensive to make. This invention is directed to providing a structure meeting such needs.

In accordance with the invention, a sculptured artificial nail is adhesively bonded to the natural nail by a bonding composition such as cyanoacrylate glue. The artificial nail includes a flexible plastic sheet, a granular material, adhesively bonded by a layer of the cyanoacrylate glue to the upper face of the plastic sheet to form a textured surface. Any granular material which can be bonded with the cyanocrylate glue, for example, ordinary table salt, sugar, glass beads, or methacrylate polymer including an appropriate catalyst may be used. If an artificial nail of additional thickness is desired, a textured layer formed of the granular material adhesively bonded to the textured surface by a layer of cyanoacrylate glue may be applied.

The invention is applied to making a sculptured artificial nail by bonding a portion of the lower face of the flexible plastic sheet to a portion of the natural nail with the cyanoacrylate glue, with the plastic sheet projecting beyond the outwardly extending end of the natural nail. The bonding composition is applied substantially only over a portion of the white-colored, outwardly extending end of the natural nail. A layer of the cyanoacrylate glue is applied to the upper face of the plastic sheet and the granular material is applied over the glue to adhesively bond the granular material to the upper face of the plastic member so as to form an artificial nail having a textured surface. If the artificial nail is to be of further thickness, a layer of the glue may be applied to the textured surface, after which the granular material is applied thereon so as to form a textured layer disposed over and in contact with the textured surface. Alternatively, the glue and the granular material may be initially pre-mixed together. A layer of this mixture may then be applied to the upper face of the plastic sheet in the same manner as hereinabove described.

In the alternate structure of the invention for making a sculptured artificial nail, a monomer/polymer composition is substituted for the granular material and the cyanoacrylate glue. The structure of the artificial nail is otherwise identical to that described above in the first structure.

In a further alternate embodiment of the invention, an artificial nail may be used to repair, strengthen or sculpture a natural nail. A layer of the cyanoacrylate glue is applied to a portion of the natural nail. The granular material is applied to the nail and is bonded thereto by the glue to form a textured surface so as to repair a damaged nail, to prevent it from breaking in the first instance or to form a textured surface on the natural nail. If the natural nail is to be of further thickness, a layer of glue may be applied to the textured surface after which the granular material is applied thereon so as to form a textured layer disposed over and in contact with the textured surface.

BRIEF DESCRIPTION OF THE DRAWINGS

FIG. 1 is a top view after the addition of bonding composition forming a part of the artificial nail in accordance with the invention;

FIG. 2 is a side view of FIG. 1;

FIG. 3 is a top view after the addition of a plastic sheet member and the bonding composition forming a part of the artificial nail;

FIG. 4 is a side view partly in section of FIG. 3;

FIG. 5 is a top view after the addition of a granular material forming a part of the artificial nail;

FIG. 6 is a side view partly in section of FIG. 5;

FIG. 7 is a side view partly in section after further addition of the granular material forming a part of the artificial nail;

FIG. 8 is a side view partly in section of the artificial nail when completed;

FIG. 9 is a side view partly in section of an alternate structure in accordance with the invention, after the addition of a monomer/polymer composition forming part of the artificial nail;

FIG. 10 is a side view partly in section of the alternate structure, when completed, of the artificial nail;

DETAILED DESCRIPTION OF THE DRAWINGS

Figure 11:
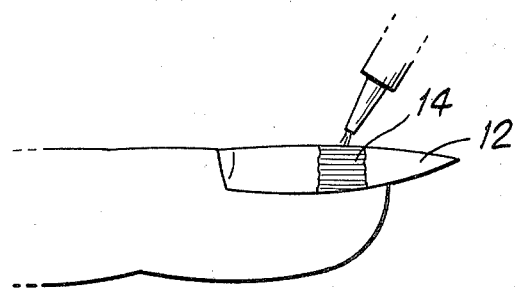
FIG. 11 is a side view of a further alternate structure in accordance with the invention, after the addition of bonding composition forming a part of the artificial nail in accordance with the invention.

Referring to FIG. 8, a sculptured artificial nail 10, is adhesively bonded to a natural nail 12 by a cyanoacrylate glue 14 (shown in FIGS. 1 and 2). The cyanoacrylate glue 14 is sold under, for example, the trademark KRISTY WELLS GLUE and is capable of curing or drying in air in about 4 to 6 seconds. The cyanoacrylate glue 14 may have a viscosity between 1 and 400 centipoises (Brookfield Viscometer). The preferred viscosity of the glue 14 is between 2 and 5 centipoises. The artificial nail 10 includes a flexible plastic sheet 16, a granular material 18 (shown best in FIGS. 5 and 6), adhesively bonded by a layer of cyanoacrylate glue 14 to the upper face of the plastic sheet 16 to form a textured surface 20. Any dry granular material 18, including a powdered material, which can be bonded with the cyanoacrylate glue 14, for example, ordinary table salt, sugar, glass beads or methacrylate polymer may be used. The choice of the granular material 18 used is dependent upon the degree of inertness desired, speed of bonding, hardness, flammability, flexibility, etc. Two particularly advantageous granular materials 18 are glass beads and methacrylate polymer including an appropriate catalyst such as benzoyl peroxide. The glass beads used by applicant are solid glass spheres, having a particle size between 0.0029 and 0.0098 inches, corresponding to U.S. Bureau of Standards Testing Sieves Nos. 60 and 200, respectively. (A test method for obtaining desired particle size is described in American Society of Testing Materials publication E11-60-T.) The preferred particle size for the glass beads is 0.0041 inches, corresponding to Sieve No. 140. The limitations on particle size are such that a too fine size, such as approaching a powder, would be ineffectual in applicant's invention, since when the glue 14 is applied thereto the glue will not settle in the granular material but will roll off. On the other hand, a granular material having a too large particle size will not provide a continuous surface layer. A further preferred granular material 18 is methacrylate polymer including an appropriate catalyst such as benzoyl peroxide. The size limitations disclosed in connection with the glass beads are also applicable to this granular material. Any plastic sheet 16 of reasonable thickness may also be used, for example, acetate, as long as it can be bonded with the cyanoacrylate glue 14. The cyanoacrylate glue 14 and the plastic sheet 16 may be selected so that they are both soluble in acetone, thereby facilitating the removal of the artificial nail 10 from the natural nail 12 by soaking therein. Additionally, while it is not necessary, the plastic sheet 16 may be preformed to conform to the contour of the upper face of the natural nail 12. The sculptured artificial nail 10 may be made to any desired thickness by applying additional textured layers 22, formed of the granular material 18 adhesively bonded to the textured surface 20 by a layer of cyanoacrylate glue 14.

One method of attaching a sculptured artificial nail to a natural nail in accordance with the invention is illustrated in FIGS. 1 through 8. As illustrated in FIGS. 1 and 2, the artificial nail 10 is initially formed by applying a drop of cyanoacrylate glue 14 on a natural nail 12. The glue 14 may be applied on any portion on the nail 12, but preferably on or near the center of the white-colored, outwardly extending end thereof, so as to leave most of the natural nail 12 free so that it may "breathe". As best seen in FIGS. 3 and 4, the plastic sheet 16 is adhesively bonded to the natural nail 12 by a drop of cyanoacrylate glue 14. The plastic sheet 16 may be bonded about 1/16 to ⅛ inch from the tip of the outwardly extending edge of the natural nail 12 so that it projects a suitable length outwardly beyond the natural nail 12. The plastic sheet 16 bonds almost instantly to the nail 12. A scissor may be used to trim the plastic sheet 16 into the approximate shape of the desired artificial nail 10. After trimming, a layer of the cyanoacrylate glue 14 is applied evenly over substantially the entire upper face of the plastic sheet 16 and possibly on the natural nail 12 where it joins the artificial nail 10.

After the layer of glue 14 is applied, as illustrated in FIGS. 5 and 6, the granular material 18 is applied to the upper face of the plastic sheet 16 and is almost instantly adhesively bonded thereto by the layer of cyanoacrylate glue 14 to form a textured surface 20. If a plastic sheet 16 of heavier thickness is used, as for example used in the Matranga et al. patent, it may not necessarily completely conform to the contour of the upper face of the natural nail 12 and thus gaps between the plastic sheet 16 and the natural nail 12 may occur. The gaps may be filled in by also applying the glue 14 and the granular material 18 between the plastic sheet 16 and the natural nail 12 and thus provide a stronger bond therebetween. To obtain a more sculptured and thicker artificial nail 10, an additional textured layer 22 may be applied. A new layer of cyanoacrylate glue 14 may be applied to the textured surface 20 and additional amounts of the granular material 18 are applied thereto to form the textured layer 22 (FIGS. 7 and 8). Additional textured layers may be added in a similar manner until the desired thickness of the artificial nail is obtained. Referring back to FIG. 8, after the desired thickness has been reached, the sculptured artificial nail 10 may be tapered back to blend into the natural nail by use of a nail file and buffer prior to being coated with nail polish. The granular material 18 and cyanoacrylate glue 14 may also be used to fill the ridge formed by the plastic sheet 16 where it joins the natural nail 12. A small amount of granular material 18 is applied to the formed ridge and a small amount of glue 14 is added. Of course, the procedure may be reversed, i.e., the glue 14 is applied to the ridge and the granular material 18 is added until the ridge is filled.

Alternatively, the glue 14 and the granular material 18 may be initially pre-mixed together. A layer of this mixture may then be applied to the upper face of the plastic sheet 16 in the same manner as hereinabove described.

In an alternate embodiment of the invention for attaching an artificial sculptured nail to a natural nail, as illustrated in FIGS. 9 and 10, the plastic sheet 16 is adhesively bonded to the natural nail 12 by the cyanoacrylate glue 14. A mixture 26 of a powdered acrylic polymer and a liquid acrylic monomer is applied to the upper face of the plastic sheet 16. An example of a monomer/polymer composition 26 is disclosed in the Sautter et al. patent. As in the first embodiment of the invention, the sculptured artificial nail 10' may be made to any desired thickness by applying additional textured layers 30 formed of the monomer/polymer composition 26.

Figure 12:
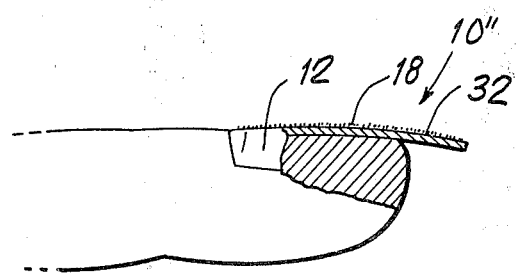
FIG. 12 is a side view partly in section of the further alternate structure, when completed, of the artificial nail.

In a further alternate embodiment of the invention, as illustrated in FIGS. 11 and 12, an artificial nail 10" may be used to repair, strengthen or sculpture the natural nail 12. A layer of the glue 14 is applied to a portion of the nail 12. The granular material 18 is then applied to the nail 12 and is almost instantly adhesively bonded thereto by the layer of glue 14 to form a textured surface 32. The extent on the nail 12 of the layer of glue 14 is dependent on whether, for example, it is desired to repair only the damaged portion of a nail or if it is to strengthen it, in which case the entire nail might be covered. To obtain a more sculptured natural nail 12, an additional textured layer may be applied in the same manner as discussed in connection with the first embodiment of the invention. Additional textured layers may be added until the desired thickness has been reached.

I claim:
1. A method of forming an artificial nail comprising:
   (a) adhesively bonding a granular material comprising methacrylate polymer granules to a substrate located in the position of a nail on a human finger by applying the granules to the substrate in the presence of sufficient cyanoacrylate glue to bond the particles to each other and to the substrate, for establishing on the substrate an adherent layer of bonded granules in which the granules impart depth to the layer and form an outwardly exposed granular surface; and
   (b) shaping the produced artificial nail to simulate the appearance of a natural nail.
2. A method of forming an artificial nail as in claim 1 wherein said substrate is a natural nail.
3. A method of forming an artificial nail as in claim 1 wherein said substrate is a plastic sheet member.
4. A method according to claim 1, wherein the shaping step includes filing.
5. A method according to claim 1, wherein the shaping step includes buffing.
6. A method according to claim 3, wherein the shaping step includes cutting the plastic sheet member to the shape of a natural nail.
7. A method according to claim 3, in which the plastic sheet member is adhered to and covers only a portion of a natural nail such that there is a ridge formed at the joinder of the sheet member and the natural nail, and wherein the applying step includes applying the granules in the presence of the glue adjacent the ridge such that said layer fills in the ridge.

* * * * *